United States Patent
Cao et al.

(10) Patent No.: US 11,511,036 B2
(45) Date of Patent: Nov. 29, 2022

(54) INFUSION PUMP AND INFUSION METHOD DEDICATED FOR STEM CELL

(71) Applicant: BEIJING ZHEN HUIKANG BIOLOGICAL TECHNOLOGY Co., Ltd., Beijing (CN)

(72) Inventors: Yulin Cao, Beijing (CN); Juntang Lin, Beijing (CN); Xiayun Li, Beijing (CN); Wei He, Beijing (CN); Shihong Liu, Beijing (CN); Chengqian Lu, Beijing (CN)

(73) Assignee: BENING ZHEN HUIKANG BIOLOGICAL TECH. Co., Ltd., Beijing (CN)

( * ) Notice: Subject to any disclaimer, the term of this patent is extended or adjusted under 35 U.S.C. 154(b) by 973 days.

(21) Appl. No.: 16/321,866

(22) PCT Filed: Aug. 11, 2016

(86) PCT No.: PCT/CN2016/094496
§ 371 (c)(1),
(2) Date: Jan. 30, 2019

(87) PCT Pub. No.: WO2018/023826
PCT Pub. Date: Feb. 8, 2018

(65) Prior Publication Data
US 2019/0175830 A1  Jun. 13, 2019

(30) Foreign Application Priority Data
Aug. 1, 2016 (CN) .......................... 201610622258.4

(51) Int. Cl.
*A61M 5/168* (2006.01)
*A61M 5/152* (2006.01)
(Continued)

(52) U.S. Cl.
CPC ......... *A61M 5/16813* (2013.01); *A61K 35/28* (2013.01); *A61L 31/028* (2013.01);
(Continued)

(58) Field of Classification Search
CPC .............................. A61M 5/14; A61M 5/152
See application file for complete search history.

(56) References Cited

U.S. PATENT DOCUMENTS 3,650,093 A * 3/1972 Rosenberg ............ A61M 5/165
96/219
2003/0135164 A1* 7/2003 Simon ............... A61M 5/16804
604/246
(Continued)

FOREIGN PATENT DOCUMENTS

CN 1030021 A 1/1989
CN 102125909 A 7/2011
(Continued)

*Primary Examiner* — Bhisma Mehta
*Assistant Examiner* — Rachel T. Smith
(74) *Attorney, Agent, or Firm* — Craft Chu PLLC; Andrew W. Chu

(57) ABSTRACT

The infusion pump for stem cells includes a liquor storage device and an infusion pipe. The inner wall of the liquor storage sac of the liquor storage device and inner walls of the infusion pipe are provided with an anionic protective film to prevent stem cells from adhering to the infusion pump by mutual repulsion between anions. The infusion method includes checking an infusion pump for integrity, losing a liquor stop clamp, injecting a mixed liquor of stem cells and medicine, covering a protective cap, opening the liquor stop clamp, closing the liquor stop clamp for use, connecting an external cone joint with a venous cannula, and then opening the liquor stop clamp. The method also includes steadily placing the liquor storage sac on a horizontal plane using an
(Continued)

auxiliary placing device, and after infusion ends, closing the liquor stop clamp, and disconnecting the external cone joint.

10 Claims, 2 Drawing Sheets

(51) Int. Cl.
    *A61K 35/28*     (2015.01)
    *A61L 31/02*     (2006.01)
    *A61L 31/04*     (2006.01)
    *A61L 33/04*     (2006.01)
    *A61L 33/06*     (2006.01)
    *A61M 5/158*     (2006.01)
    *A61M 16/08*     (2006.01)

(52) U.S. Cl.
    CPC ............ *A61L 31/042* (2013.01); *A61L 33/04* (2013.01); *A61L 33/064* (2013.01); *A61L 33/068* (2013.01); *A61M 5/152* (2013.01); *A61M 5/158* (2013.01); *A61M 16/0816* (2013.01)

(56) References Cited

U.S. PATENT DOCUMENTS

| | | | | |
|---|---|---|---|---|
| 2006/0015071 | A1* | 1/2006 | Fitzgerald | A61M 25/0693 604/164.01 |
| 2013/0018326 | A1* | 1/2013 | Hooven | A61M 5/14248 604/198 |
| 2017/0326294 | A1* | 11/2017 | Kato | A61M 39/284 |
| 2018/0008768 | A1* | 1/2018 | Prescher | A61M 5/152 |
| 2019/0365988 | A1* | 12/2019 | Kim | A61M 5/16822 |

FOREIGN PATENT DOCUMENTS

| | | | | |
|---|---|---|---|---|
| CN | 102783952 | A | 11/2012 | |
| CN | 204958920 | * | 1/2016 | |
| CN | 204958920 | U | 1/2016 | |
| EP | 0452912 | A2 * | 4/1991 | |
| EP | 2407533 | A1 * | 1/2012 | ............ C12M 23/04 |
| FR | 2488854 | * | 8/1980 | ........... G01N 33/491 |
| GB | 1495856 | * | 2/1975 | |
| JP | 2004018504 | A | 1/2004 | |

\* cited by examiner

INFUSION PUMP AND INFUSION METHOD DEDICATED FOR STEM CELL

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to the field of medical apparatus and instruments, particularly to a special infusion pump for stem cells and an infusion method therefor.

2. Description of Related Art Including Information Disclosed Under 37 CFR 1.97 and 37 CFR 1.98.

For a long time, because of considering that postoperative pain is a natural phenomenon and is inevitable, people can only endure postoperative pain in silence. In fact, pain can produce a series of pathological and physiological changes, for example, the effects of the body's autonomic nervous system, which cause heart rate acceleration, shortness of breath, and blood pressure increment; mental changes, which lead to irritability and depression, and then affect digestive system function and physical recovery; the effects on endocrine and hormones, which directly and indirectly change the functions of various receptors. Until the 1970s, an infusion pump (analgesia pump) was developed, the infusion pump being an electronically controlled injection device that allows constant-speed intravenous injection of pain killers at a preset rate, makes pain killers maintain a timely and stable concentration in plasma, and allows the patient to automatically press for administration to quickly enhance the effect, making the treatment more individualized.

Stem cells are a kind of multi-potential cell with self-renewing capability, which can be divided into multiple functional cells under certain conditions. A stem cell is a cell which is not fully differentiated and is not mature, has the potential function of regenerating various tissue and organ and human body, and is referred to as "universal cell" in the medical field. It is found through clinical treatment that the injection of stem cells plays an extremely beneficial effect on many diseases and postoperative recovery. But it is found in the actual treatment course that because the biggest difference between cells and the traditional physic liquor is that cells have activity, if stem cells are infused by a traditional infusion pump, many cells may adhere to the inner wall of the liquor storage cavity and the infusion pipe, directly causing a great discount on the infusion effect, and then causing waste of precious stem cells.

BRIEF SUMMARY OF THE INVENTION

To solve the problem that stem cells may adhere to the inner wall of the liquor storage cavity and the infusion pipe, which may be caused if the existing infusion pump is used for stem cell infusion, the present invention provides a special infusion pump for stem cells and an infusion method therefor, and adopts the specific solution as follows:

A special infusion pump for stem cells, comprising: a liquor storage device and an infusion pipe, wherein the liquor storage device includes a protective housing in which a cavity structure is formed and a liquor storage sac disposed in the protective housing, wherein the bottom of the protective housing is provided with a through hole, the infusion pipe is connected with the liquor storage sac through the through hole, the infusion pipe is provided with a medicine infusion port, a liquor stop clamp, a flow control device and an external cone joint in sequence from the end close to the liquor storage device to the end far away from the liquor storage device; and the inner wall of the liquor storage sac and the infusion pipe is provided with a layer of anionic protective film.

Further, the liquor storage sac is made of silicon rubber, so that the liquor storage sac has good elasticity, and the physic liquor is infused into the body of a patient using the recoil of the liquor storage sac without external force in the process of normal operation.

Further, the size of the cavity structure in the protective housing is greater than the minimum deformation size of the liquor storage sac, and the size of the cavity structure in the protective housing is less than the maximum deformation size of the liquor storage sac, so that the liquor storage sac has a deformation space in the cavity of the protective housing, which has a fixed size and does not exceed the maximum deformation size thereof.

Further, the medicine infusion port is externally provided with a one-way check valve used to guarantee that the operator can add physic liquor into the pump through the medicine infusion port but the physic liquor in the pump cannot flow out from the medicine infusion port, and the one-way check valve is provided with a protective cap used to prevent physic liquor from being polluted.

Further, the protective housing is provided with an auxiliary placing device used to steadily place or hang the protective housing together with the liquor storage sac in a certain position, to guarantee the stability of the pump during operation.

Further, the anionic protective film includes a substrate. In further improvement, an anticoagulation layer is stacked on one side surface of the substrate.

In further improvement, the substrate is prepared from components of the following part by weight: 20-30 parts by weight of polyvinyl resin, 6-12 parts by weight of tourmaline powder, 0.5-0.7 part by weight of methylcellulose and 0.3-0.6 part by weight of polymethacrylic acid.

Preferably, the anticoagulation layer is prepared from components of the following part by weight: 7.5-10 parts by weight of cholesteryl palmitate, 3.5-5 parts by weight of sodium oleate, 1-3 parts by weight of sodium stearyl lactate, and 0.2-0.5 part by weight of sodium stearate.

The anionic protective film provided by the present invention is mainly composed of a substrate and an adhesion layer and an anticoagulation layer respectively stacked on two side surfaces of the substrate, and the components of the substrate and the anticoagulation layer are further defined, so that the anionic protective film may not affect the activity of the stored stem cells.

Further, the protective housing, the one-way check valve, the liquor stop clamp, the flow control device and the external cone joint are made of medical-level PP plastics, thereby guaranteeing the physical performance while guaranteeing the safety and sanitation thereof; and the infusion pipe is made of medical-level PVC plastics, so that the pipe material may not react with the physic liquor, is safe and sanitary, moreover, and is transparent, thereby facilitating clinical observation of medical staff.

Further, the infusion pump also comprises a medicine inhalation device matching with same, which can recycle physic liquor in the pump after infusion ends as required.

An infusion method for stem cells, comprising the following steps:

Step 1. carefully checking each working component of an infusion pump for integrity;

Step 2. closing a liquor stop clamp, taking off a protective cap, and injecting a pre-prepared mixed liquor of stem cells and medicine into the liquor storage sac by an injector or other auxiliary device through the medicine infusion port;

Step 3. covering the protective cap, opening the liquor stop clamp, until no bubble exists in the infusion pump, closing the liquor stop clamp for use;

Step 4. connecting an external cone joint with a venous cannula in the body of a patient to be infused, and then opening the liquor stop clamp, to guarantee that the mixed liquor of the stem cells and the medicine is infused into the body of the patient using the uniform elastic recoil of the liquor storage sac in cooperation with the action of the flow control device;

Step 5. steadily placing the liquor storage sac on a horizontal plane or hanging same in a certain position using an auxiliary placing device disposed on the protective housing;

Step 6. after infusion ends, closing the liquor stop clamp first, and then disconnecting the external cone joint from the venous cannula in the body of the patient; and Step 7. inhaling the remaining physic liquor from the external cone joint by a medicine inhalation device.

The present invention has the advantageous effects that: by means of the special infusion pump for stem cells and the infusion method therefor proposed the present invention, the elastic recoil of the liquor storage sac is used as driving power to drive the mixed liquor of stem cells and medicine to be infused into the human body through an infusion pipe in cooperation with the flow control device, because the inner wall of the liquor storage sac and the infusion pipe is provided with a layer of anionic protective film which produces like polarity repelling effect on phospholipid bilayer with negative charge of the basic structure of the stem cell membrane, the loss of stem cells caused by adhering to the wall in the process of infusion is greatly reduced.

Figure 1:
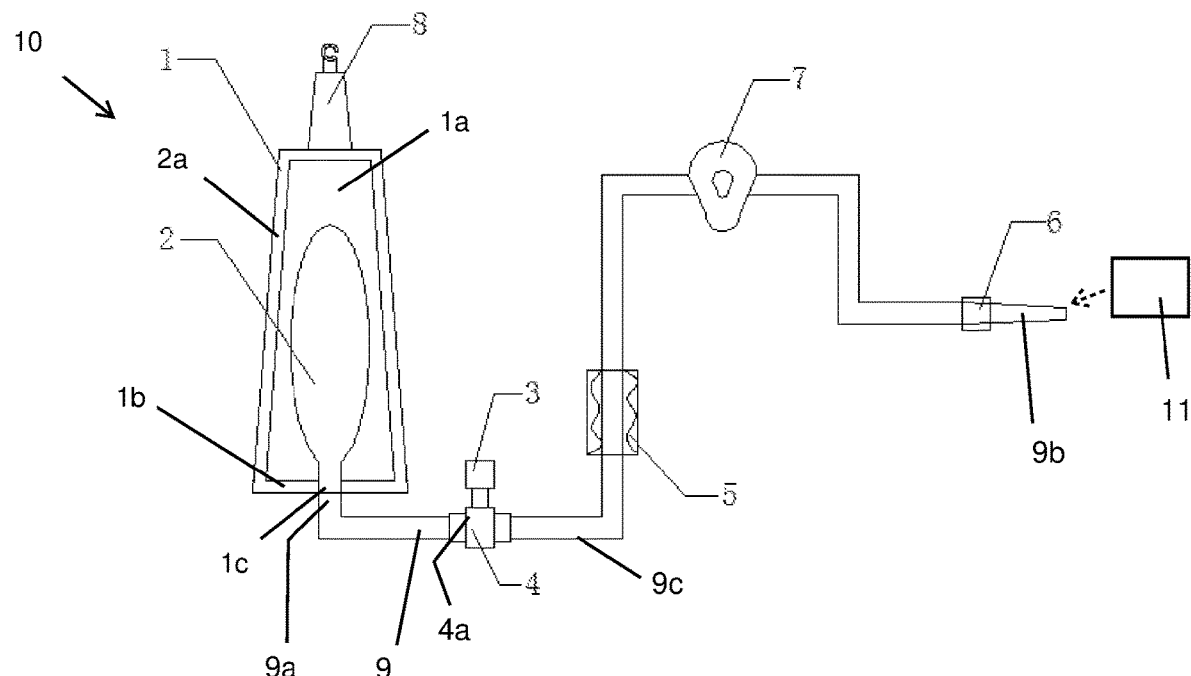
FIG. 1 is a structural schematic view of an infusion pump of the present invention.

Reference numeral: 1. protective housing; 2. liquor storage sac; 21. anionic protective film; 3. protective cap; 4. one-way check valve; 5. liquor stop clamp; 6. external cone joint; 7. flow control device; 8. auxiliary placing device.

DETAILED DESCRIPTION OF THE INVENTION

In order to explain in detail the technical contents, structural features, objects and effects of the present invention, the present invention is described below in detail with reference to embodiments and the drawings.

Embodiment 1

Figure 2:
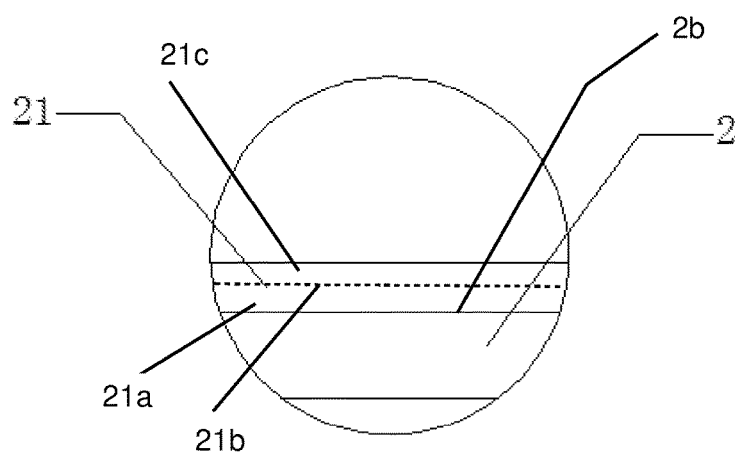
FIG. 2 is an enlarged schematic view of an inner wall structure of a liquor storage sac and an infusion pipe of the present invention.

Referring to FIG. 1 and FIG. 2, the present invention provides a special infusion pump 10 for stem cells, comprising: a liquor storage device 2a and an infusion pipe 9. The liquor storage device includes a protective housing 1 in which a columnar cavity 1a structure is formed and a liquor storage sac 2 disposed in the protective housing. The bottom end 1b of the protective housing 1 is provided with a through hole 1c communication with the liquor storage sac 2. The infusion pipe (having a proximal pipe and 9a, a distal pipe end 9b oppoisite the proximal pipe end, and a pipe inner wall 9c) is in communication with the through hole 1c at the bottom end 1b of the protective housing 1. The infusion pipe is provided with a medicine infusion port 4a, a liquor stop clamp 5, a flow control device 7 and an external cone joint 6 in sequence from the proximal pipe end 9a close to the liquor storage device 2a to the distal pipe end 9b far away from the liquor storage device. There is a sac inner wall 2b of the liquor storage sac 2. The sac inner wall 2b and the infusion pipe are provided with a layer of anionic protective film 21. Being made of silicone rubber, the liquor storage sac 2 has good elasticity. The liquor is infused into the body of the patient using the recoil of the liquor storage sac without external force in the process of normal operation. The size of the cavity structure 1a in the protective housing 1 is greater than the minimum deformation size of the liquor storage sac 2, and the size of the cavity structure 1a in the protective housing 1 is less than the maximum deformation size of the liquor storage sac 2, so that the liquor storage sac 2 has a deformation space in the cavity structure 1a of the protective housing 1, which has a fixed size and does not exceed the maximum deformation size thereof.

The medicine infusion port 4a is externally provided with a one-way check valve 4, so that liquor can only be injected into the infusion pump through the medicine infusion port 4a but cannot flow out from the medicine infusion port 4a. Moreover, the one-way check valve 4 is provided with a protective cap 3 used to prevent liquor from being polluted. The protective housing 1 is provided with an auxiliary placing device 8, the auxiliary placing device 8 being a hook or support leg arranged on the housing and being used to steadily place or hang the protective housing 1 together with the liquor storage sac 2 in a certain position, to guarantee the stability of the pump during operation. The infusion pipe is made of medical grade polyvinyl chloride PVC plastics, so that the pipe material may not react with the physic liquor, is safe and sanitary, and is transparent, thereby facilitating clinical observation of medical staff. The protective housing 1, the one-way check valve 4, the liquor stop clamp 5, the flow control device 7 and the external cone joint 6 are made of medical grade polypropylende plastics, thereby guaranteeing certain strength thereof while guaranteeing the safety and sanitation thereof, and guaranteeing the normal operation of the infusion pump.

Figure 3:
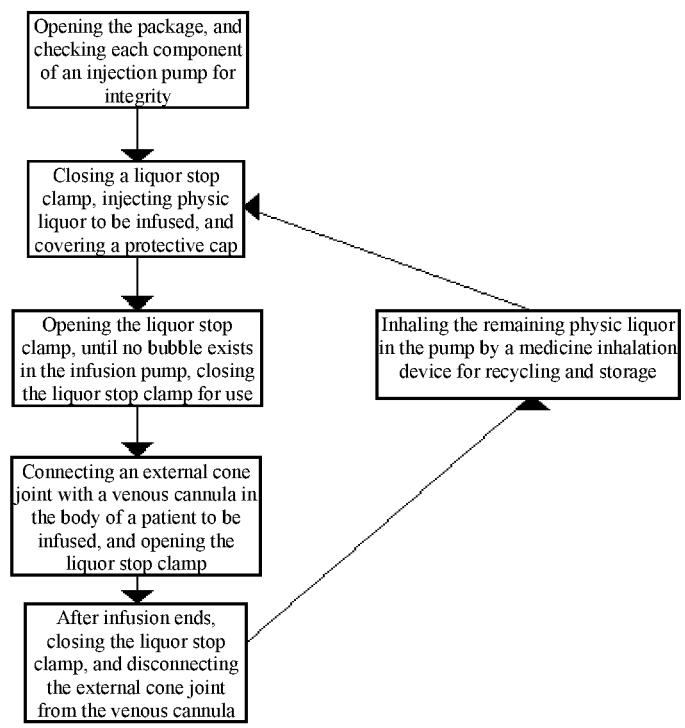
FIG. 3 is a flow diagram of an infusion method of the present invention.

As shown in FIG. 3, carefully checking each working component of an infusion pump for integrity; closing a liquor stop clamp, taking off a protective cap, and injecting a pre-prepared mixed liquor of stem cells and medicine into the liquor storage sac by an injector and other auxiliary device through the medicine infusion port; covering the protective cap, opening the liquor stop clamp, until no bubble exists in the infusion pump, closing the liquor stop clamp for use; connecting an external cone joint with a venous cannula in the body of a patient to be infused, and then opening the liquor stop clamp, to guarantee that the mixed liquor of the stem cells and the medicine is infused into the body of the patient using the uniform elastic recoil of the liquor storage sac in cooperation with the action of the flow control device; steadily placing the liquor storage sac on a horizontal plane or hanging same in a certain position using an auxiliary placing device disposed on the protective housing; after infusion ends, closing the liquor stop clamp first, and then disconnecting the external cone joint from the venous cannula in the body of the patient; inhaling the remaining physic liquor from the external cone joint by a medicine inhalation device 11; and destroying the used infusion pump in accordance with the disposal method for medical waste strictly.

Embodiment 2

A special infusion pump for stem cells, the infusion pump is different from embodiment 1 in that the anionic protective film includes a substrate prepared from components of the following part by weight: 20 parts by weight of polyvinyl resin, 6 parts by weight of tourmaline powder, 0.5 part by weight of methylcellulose and 0.3 part by weight of polymethacrylic acid. The anionic protective film is extruded into a polyethylene self-adhesive film together with micro-adhesive EVA. Because the film is mixed with tourmaline powder in the making process, the protective film can release anions. Because the basic structure of the cell membrane is a bilayer composed of phospholipids, and the phosphorus-containing portion of the phospholipid molecules carries negative charge, stem cells in the physic liquor are prevented from adhering to the inner wall of the liquor storage sac 2 and the pipe using the effect "like charges repel each other".

Embodiment 3

A special infusion pump for stem cells, the infusion pump is different from embodiment 2 in that the substrate is prepared from components of the following part by weight: 25 parts by weight of polyvinyl resin, 8 parts by weight of tourmaline powder, 0.6 part by weight of methylcellulose and 0.4 part by weight of polymethacrylic acid.

Embodiment 4

A special infusion pump for stem cells, the infusion pump is different from embodiment 2 in that the substrate is prepared from components of the following part by weight: 30 parts by weight of polyvinyl resin, 12 parts by weight of tourmaline powder, 0.7 part by weight of methylcellulose and 0.6 part by weight of polymethacrylic acid.

Embodiment 5

A special infusion pump for stem cells, the infusion pump is different from embodiment 2 in that an anti-coagulation layer 21c is stacked on one side surface 21b of the substrate 21a, the anticoagulation layer being prepared from components of the following part by weight: 7.5 parts by weight of cholesteryl palmitate, 3.5 parts by weight of sodium citrate, 1 part by weight of sodium stearoyl lactylate and 0.2 part by weight of sodium stearate.

Embodiment 6

A special infusion pump for stem cells, the infusion pump is different from embodiment 2 in that an anticoagulation layer is stacked on one side surface of the substrate, the anticoagulation layer being prepared from components of the following part by weight: 8.7 parts by weight of cholesteryl palmitate, 4.2 parts by weight of sodium citrate, 2 parts by weight of sodium stearoyl lactylate and 0.3 part by weight of sodium stearate.

Embodiment 7

A special infusion pump for stem cells, the infusion pump is different from embodiment 2 in that an anticoagulation layer is stacked on one side surface of the substrate, the anticoagulation layer being prepared from components of the following part by weight: 10 parts by weight of cholesteryl palmitate, 5 parts by weight of sodium citrate, 3 parts by weight of sodium stearoyl lactylate and 0.5 part by weight of sodium stearate.

Both the substrate and anticoagulation layer are prepared by means of the conventional method.

Control Group 1

A special infusion pump for stem cells, the infusion pump is different from embodiment 2 in that the substrate is prepared from components of the following part by weight: 10 parts by weight of polyvinyl resin, 13 parts by weight of tourmaline powder, 0.4 part by weight of methylcellulose and 0.7 part by weight of polymethacrylic acid.

Control Group 2

A special infusion pump for stem cells, the infusion pump is different from embodiment 2 in that the substrate is prepared from components of the following part by weight: 25 parts by weight of polyvinyl resin, 0.5 part by weight of methylcellulose and 0.3 part by weight of polymethacrylic acid.

Control Group 3

A special infusion pump for stem cells, the infusion pump is different from embodiment 2 in that the substrate is prepared from components of the following part by weight: 20 parts by weight of epoxy resin, 6 parts by weight of tourmaline powder, 0.5 part by weight of methylcellulose and 0.3 part by weight of polymethacrylic acid.

Control Group 4

A special infusion pump for stem cells, the infusion pump is different from embodiment 2 in that the substrate is prepared from components of the following part by weight: 20 parts by weight of polyvinyl resin, 15 parts by weight of tourmaline powder, 0.5 part by weight of methylcellulose and 0.3 part by weight of polymethacrylic acid.

Control Group 5

A special infusion pump for stem cells, the infusion pump is different from embodiment 2 in that the substrate is prepared from components of the following part by weight: 20 parts by weight of polyvinyl resin, 6 parts by weight of tourmaline powder, 0.4 part by weight of methylcellulose and 0.3 part by weight of polymethacrylic acid.

Control Group 6

A special infusion pump for stem cells, the infusion pump is different from embodiment 2 in that the substrate is prepared from components of the following part by weight: 20 parts by weight of polyvinyl resin, 6 parts by weight of tourmaline powder, 0.8 part by weight of methylcellulose and 0.3 part by weight of polymethacrylic acid.

Control Group 7

A special infusion pump for stem cells, the infusion pump is different from embodiment 2 in that the substrate is prepared from components of the following part by weight: 20 parts by weight of polyvinyl resin, 6 parts by weight of tourmaline powder, 0.5 part by weight of methylcellulose and 0.2 part by weight of polymethacrylic acid.

Control Group 8

A special infusion pump for stem cells, the infusion pump is different from embodiment 2 in that the substrate is prepared from components of the following part by weight: 20 parts by weight of polyvinyl resin, 6 parts by weight of tourmaline powder, 0.5 part by weight of methylcellulose and 0.7 part by weight of polymethacrylic acid.

Control Group 9

A special infusion pump for stem cells, the infusion pump is different from embodiment 5 in that the anticoagulation layer is prepared from components of the following part by weight: 6 parts by weight of cholesteryl palmitate, 5.5 parts by weight of sodium citrate, 0.8 part by weight of sodium stearoyl lactylate and 0.6 part by weight of sodium stearate.

Control Group 10

A special infusion pump for stem cells, the infusion pump is different from embodiment 5 in that the anticoagulation layer is prepared from components of the following part by weight: 3.5 parts by weight of sodium oleate, 1 part by weight of sodium stearoyl lactylate and 0.2 part by weight of sodium stearate.

Control Group 11

A special infusion pump for stem cells, the infusion pump is different from embodiment 5 in that the anticoagulation layer is prepared from components of the following part by weight: 7.5 parts by weight of cholesteryl palmitate, 3.5 parts by weight of sodium citrate and 1 part by weight of sodium stearoyl lactylate.

Test Example 1

Infuse stem cells using infusion pumps for stem cells in embodiment 2-4 and control groups 1-8 respectively, and count the infusion rate of stem cells. See Table 1 for results.

TABLE 1

Results of infusion rate of infusion pumps for stem cell of all embodiments and control examples

| Group | Stem cell infusion rate |
|---|---|
| Embodiment 1 | 94.3 |
| Embodiment 2 | 97.6 |
| Embodiment 3 | 95.0 |
| Control group 1 | 57.1 |
| Control group 2 | 62.7 |

TABLE 1-continued

Results of infusion rate of infusion pumps for stem cell of all embodiments and control examples

| Group | Stem cell infusion rate |
|---|---|
| Control group 3 | 66.8 |
| Control group 4 | 76.3 |
| Control group 5 | 77.5 |
| Control group 6 | 75.4 |
| Control group 7 | 73.2 |
| Control group 8 | 69.4 |

As shown in the Table, the substrate of the anionic protective film prepared from polyvinyl resin, tourmaline powder, methylcellulose and polymethacrylic acid provided by the present invention may prevent stem cells in the physic liquor from adhering to the inner wall of the liquor storage sac and the pipe using the effect "like charges repel each other", thereby guaranteeing the infusion rate of stem cells, and if parts by weight of polyvinyl resin, tourmaline powder, methylcellulose and polymethacrylic acid are not within the scope of the present invention or the components thereof are replaced or one of the components is omitted, the infusion rate of stem cells may be affected.

Test Example 2

Observe time when protein precipitation occurs and time when hemolysis occurs in blood of stem cells infused in infusion pumps for stem cells of embodiments 5-7 and control groups 9-11. See Table 2 for results.

TABLE 2

Time when protein precipitation occurs and time when hemolysis occurs in stem cells in infusion pumps for stem cells of all embodiments and control examples

| Group | Time when protein precipitation occurs h | Time when hemolysis occurs h |
|---|---|---|
| Embodiment 4 | 58 | 44 |
| Embodiment 5 | 71 | 61 |
| Embodiment 6 | 63 | 50 |
| Control group 9 | 26 | 19 |
| Control group 10 | 18 | 12 |
| Control group 11 | 15 | 11 |

As shown in the Table, the anticoagulation layer prepared from cholesteryl palmitate, sodium oleate, sodium stearoyl lactylate, sodium lactate provided by the present invention can prevent blood in stem cells from coagulating, and can prolong the time when protein precipitation occurs and time when hemolysis occurs in blood to 71 h and 61 h to a maximum extent, and the anticoagulation effect can be greatly reduced when the parts by weight of cholesteryl palmitate, sodium oleate, sodium stearoyl lactylate and sodium stearate are too large or too small or the components are changed.

The above is just one preferred embodiment of the present invention and is not intended to limit the protection range of the present invention. All equal modifications and decorations made in accordance with the scope of the patent of the present invention shall still belong to the scope of the patent of the present invention.

We claim:

1. An infusion pump for stem cells, comprising:
a liquor storage device comprised of:

a protective housing having a cavity structure and a bottom end with a through hole; and
a liquor storage sac disposed in said protective housing and having a sac inner wall;
an infusion pipe having a proximal pipe end, a distal pipe end opposite said proximal pipe end, and a pipe inner wall, said infusion pipe being connected with said liquor storage sac through said through hole at said proximal pipe end;
a medicine infusion port in fluid connection with said infusion pipe;
a liquor stop clamp in fluid connection with said infusion pipe, said medicine infusion port being between said proximal pipe end and said liquor stop clamp;
a flow control device in fluid connection with said infusion pipe, said liquor stop clamp being between said medicine infusion port and said flow control device;
an external cone joint in fluid connection with said infusion pipe and being between said distal pipe end and said flow control device; and
an anionic protective film layered on said sac inner wall and said pipe inner wall,
wherein said anionic protective film is comprised of: a substrate with a side surface, and an anti-coagulation layer on said side surface so as to set an infusion rate of active stem cells, while preventing adherence of stem cells to said sac inner wall and said pipe inner wall,
wherein said substrate is a composition being comprised of: 20-30 parts by weight of polyvinyl resin, 6-12 parts by weight of tourmaline powder, 0.5-0.7 part by weight of methylcellulose and 0.3-0.6 part by weight of polymethacrylic acid; and
wherein said anti-coagulation layer is another composition being comprised of: 7.5-10 parts by weight of cholesteryl palm itate, 3.5-5 parts by weight of sodium oleate, 1-3 parts by weight of sodium stearyl lactate, and 0.2-0.5 part by weight of sodium stearate.

2. The infusion pump for stem cells, according to claim 1, wherein said liquor storage sac is comprised of silicone rubber.

3. The infusion pump for stem cells, according to claim 1, wherein said liquor storage sac has a minimum deformation size and a maximum deformation size, and wherein cavity structure has a cavity size greater than said minimum deformation size and less than said maximum deformation size.

4. The infusion pump for stem cells, according to claim 1, wherein said medicine infusion port is comprised of a one-way check valve with a protective cap.

5. The infusion pump for stem cells, according to claim 4, wherein said protective housing is comprised of medical grade polypropylene plastics, wherein said one-way check valve is comprised of medical grade polypropylene plastics, wherein said liquor stop clamp is comprised of medical grade polypropylene plastics, wherein said flow control device is comprised of medical grade polypropylene plastics, wherein said external cone joint is comprised of medical grade polypropylene plastics, and wherein said infusion pipe is comprised of medical grade polyvinyl chloride plastics.

6. The infusion pump for stem cells, according to claim 1, wherein said protective housing is comprised of an auxiliary placing device.

7. The infusion pump for stem cells, according to claim 1, further comprising: a medicine inhalation device removably attached to said distal pipe end so as to recycle liquor from said external cone bint.

8. An infusion method for stem cells, the method comprising the steps of:
Step 1. checking said infusion pump, according to claim 4;
Step 2.
closing a said liquor stop clamp,
taking off a said protective cap, and
injecting a pre-prepared mixed liquor of stem cells and medicine into the said liquor storage sac by an injector through said medicine infusion port;
Step 3.
covering said protective cap,
opening the said liquor stop clamp, until there are no bubbles in said infusion pump, and
closing the said liquor stop clamp;
Step 4.
connecting said external cone joint and said distal pipe end with a venous cannula so as to infuse a patient, and
opening said liquor stop clamp and using a uniform elastic recoil of liquor storage sac in cooperation with an action of said flow control device so as to guarantee that the mixed liquor is infused;
Step 5.
steadily placing said liquor storage sac in a certain position;
Step 6.
after infusion ends, closing said liquor stop clamp first, and then disconnecting said external cone joint from said venous cannula; and
Step 7.
inhaling residual liquor from said external cone joint by a medicine inhalation device.

9. The infusion method, according to claim 8, wherein said certain position is a horizontal plane in Step 5.

10. The infusion method, according to claim 8, wherein Step 5 is comprised of:
steadily placing saki liquor storage sac in a certain position with an auxiliary placing device disposed on said protective housing.

* * * * *